(12) United States Patent
Freiden et al.

(10) Patent No.: US 12,053,263 B2
(45) Date of Patent: Aug. 6, 2024

(54) DYNAMIC CALIBRATION OF LIGHT INTENSITY IN A SYSTEM FOR NON-INVASIVE DETECTION OF SKIN CANCER USING ELASTIC SCATTERING SPECTROSCOPY

(71) Applicant: DermaSensor, Inc., Miami, FL (US)

(72) Inventors: Steven Ryan Freiden, Orlando, FL (US); Warren Stewart Macchi, Orlando, FL (US); Cody Vance Simmons, Gainesville, FL (US)

(73) Assignee: DERMASENSOR, INC., Miami, FL (US)

( * ) Notice: Subject to any disclaimer, the term of this patent is extended or adjusted under 35 U.S.C. 154(b) by 259 days.

(21) Appl. No.: 17/327,317

(22) Filed: May 21, 2021

(65) Prior Publication Data

US 2022/0378295 A1     Dec. 1, 2022

(51) Int. Cl.
*A61B 5/00*     (2006.01)
(52) U.S. Cl.
CPC ............ *A61B 5/0075* (2013.01); *A61B 5/444* (2013.01); *A61B 5/6843* (2013.01); *A61B 2560/0233* (2013.01); *A61B 2560/0238* (2013.01)
(58) Field of Classification Search
None
See application file for complete search history.

(56) References Cited

U.S. PATENT DOCUMENTS 5,175,697 A    12/1992 Kawagoe et al.
5,522,868 A     6/1996 Buckley et al.
(Continued)

FOREIGN PATENT DOCUMENTS

KR    10-2019-0024298 A    3/2019
WO         99/45838 A1     9/1999

OTHER PUBLICATIONS

International Search Report and the Written Opinion of the International Searching Authority received in related International Application No. PCT/US2022/030115 dated Sep. 8, 2022.
(Continued)

*Primary Examiner* — Katherine L Fernandez
*Assistant Examiner* — Michael S Kellogg
(74) *Attorney, Agent, or Firm* — The Marbury Law Group PLLC (57) ABSTRACT

Methods and devices are disclosed for calibrating intensity of a light source in a system of evaluating a skin lesion using Elastic-Scattering Spectroscopy (ESS). The ESS system may illuminate a sample of the skin lesion with a pulse from the light source adjusted to a high output setting, receive a signal comprising an elastic scattering spectrum from illuminating the skin lesion sample at the high output setting, determine whether the received signal has an intensity that is greater than a saturation threshold associated with at least one optical detection sensor, and if so, store the elastic scattering spectrum from illuminating the skin lesion sample at the high output setting. If not greater than the saturation threshold, the ESS system may illuminate the skin lesion sample with a pulse from the light source adjusted to a low output setting, receive a signal comprising an elastic scattering spectrum from illuminating the skin lesion sample at the low output setting, and store the elastic scattering spectrum from illuminating the skin lesion sample at the low output setting.

19 Claims, 7 Drawing Sheets

(56) References Cited

U.S. PATENT DOCUMENTS

| | | | |
|---|---|---|---|
| 5,555,885 | A | 9/1996 | Chance |
| 5,822,072 | A | 10/1998 | Dai et al. |
| 6,014,204 | A | 1/2000 | Prahl et al. |
| 6,015,969 | A | 1/2000 | Nathel et al. |
| 6,165,170 | A | 12/2000 | Wynne et al. |
| 6,381,018 | B1 | 4/2002 | Bigio et al. |
| 6,792,137 | B2 | 9/2004 | Kenet |
| 7,822,468 | B2 | 10/2010 | Stamnes et al. |
| 9,072,428 | B2 | 7/2015 | Bigio et al. |
| 9,091,637 | B2 | 7/2015 | Yu et al. |
| 2002/0183624 | A1 | 12/2002 | Rowe et al. |
| 2004/0161804 | A1 | 8/2004 | McCash et al. |
| 2006/0056589 | A1 | 3/2006 | Engelward |
| 2006/0209200 | A1 | 9/2006 | Xu |
| 2006/0281068 | A1 | 12/2006 | Maier et al. |
| 2007/0073156 | A1 | 3/2007 | Zilberman et al. |
| 2009/0245603 | A1 | 10/2009 | Koruga et al. |
| 2010/0185064 | A1 | 7/2010 | Bandic et al. |
| 2011/0261355 | A1 | 10/2011 | Hannel et al. |
| 2011/0301441 | A1 | 12/2011 | Bandic et al. |
| 2012/0321759 | A1 | 12/2012 | Marinkovich et al. |
| 2015/0287191 | A1 | 10/2015 | Koruga et al. |
| 2018/0055368 | A1 | 3/2018 | Noto et al. |

OTHER PUBLICATIONS

A'Amar et al., "Comparison between ultraviolet-visible and near-infrared elastic scattering spectroscopy of chemically induced melanomas in an animal model", Journal of Biomedical Optics vol. 9, No. 6, pp. 1320-1326, (Nov./Dec. 2004).

Marchesini et al., "In vivo Spectrophotometric Evaluation of Neoplastic and Non-Neoplastic Skin Pigmented Lesions—I. Reflectance Measurements", Photochemistry and Photobiology, vol. 53, No. 1, pp. 77-84, (1991).

Marchesini et al., "In vivo Spectrophotometric Evaluation of Neoplastic and Non-Neoplastic Skin Pigmented Lesions. II: Discriminant Analysis Between Nevus and Melanoma", Photochemistry and Photobiology, vol. 55, No. 4, pp. 515-522, (1992).

Perelman et al., "Observation of Periodic Fine Structure in Reflectance from Biological Tissue: a New Technique for Measuring Nuclear Size Distribution", Physical Review Letters, vol. 80, No. 3, pp. 627-630, (Jan. 19, 1998).

Wallace et al., "Spectrophotometric assessment of pigmented skin lesions: methods and feature selection for evaluation of diagnostic performance", Phys. Med. Biol. 45, pp. 735-751, (2000).

Wolbarsht et al., "Melanin, a unique biological absorber", Appl. Opt., vol. 20, No. 13, pp. 2174-2186, (Jul. 1, 1981).

Zonios et al., "Diffuse reflectance spectroscopy of human adenomatous colon polyps in vivo", Applied Optics, vol. 38, No. 31, pp. 6628-6637, (Nov. 1, 1999).

Canpolat et al., "Diagnosis and Demarcation of Skin Malignancy Using Elastic Light Singe-Scattering Spectroscopy: a Pilot Study," Proceedings of SPIE—the International Society for Optical Engineering Jun. 2007, ResearchGate, pp. 215-223, (2012).

Prince et al., "Analysis of Spectroscopic Diffuse Reflectance Plots for Different Skin Conditions," Spectrscopy, vol. 24, pp. 467-481, (2010).

Egawa, et al., Comparison of the depth profiles of water and water binding substances in the stratum corneum determined in vivo by Raman spectroscopy between the cheek and volar forearm: effects of age, seasonal changes and artificial forced hydration, Clinical and Laboratory Investigations, Br. J. Dermatol; 158: 251-60, (2008).

International Preliminary Report on Patentability and Written Opinion of the International Searching Authority recieved from the International Bureau of WIPO in related International Application No. PCT/US2022/030115 dated Nov. 30, 2023.

DYNAMIC CALIBRATION OF LIGHT INTENSITY IN A SYSTEM FOR NON-INVASIVE DETECTION OF SKIN CANCER USING ELASTIC SCATTERING SPECTROSCOPY

BACKGROUND OF THE INVENTION

Skin cancer is the most common cancer in humans in the United States, and may be either a non-melanoma skin cancer (e.g., basal-cell, squamous-cell, and other less common skin cancers) or melanoma. While non-melanoma skin cancers may appear discolored, they are often non-pigmented. Conversely, melanomas are typically pigmented, but occasionally may appear non-pigmented compared to surrounding skin. Melanomas are the most aggressive of skin cancers, with a mortality rate that has grown over the past 20 years in most parts of the world, and squamous cell carcinomas are now estimated to have a greater mortality rate than melanomas.

Successful treatment of skin cancer depends on early diagnosis through biopsy. Prior to biopsy the screening accuracy of identifying a skin lesion as potentially malignant or benign depends essentially on the practitioner expertise. Clinical evaluation of potential skin cancers has historically been primarily based on visual features of the suspected lesions (e.g. the asymmetry, border, color, dimension, and evolution over time), which may be analyzed through visual inspection of the lesion itself or images of the lesion.

In recent years, optical spectroscopy techniques have been explored as methods for distinguishing between different tissue pathologies, including suspected cancerous lesions on the skin. These techniques may reduce the need for surgical removal of biopsy tissue samples. Instead, spectral analysis of the tissue is applied to measurements and/or recordings obtained with an optical probe placed on or near the surface of the tissue in question. Real-time diagnosis of the tissue or assessing the tissue for risk of being malignant may be attempted based on these measurements and/or recordings. Such spectroscopic techniques may include, but are not limited to, Raman spectroscopy, autofluorescence spectroscopy, fluorescence spectroscopy, reflectance spectroscopy, and elastic-scattering spectroscopy (ESS).

In particular, improved detection of potential skin cancer using ESS, either alone or in combination with image analysis, may provide data sensitive to changes of the underlying tissue. Classifier algorithms may be applied to such data. Specifically, ESS is sensitive to the wavelength dependence of the tissue optical scattering properties, which vary due to changes at the cellular and sub-cellular level as a result of the different pathologies. These changes influence the measured spectral signatures and can be used to screen for melanoma and non-melanoma skin cancers.

However, different tissue samples generally provide different levels of light absorption, and therefore the intensity of the overall backscattered signal may vary from sample to sample. Depending on the properties of the optical detection component(s), (e.g., sensor(s)), such variation may negatively affect the quality of the spectral data that is recorded by the system. For example, if the amount of light received by the detector is too great, some of the spectral measurements and/or recordings may not be entirely captured resulting in compromised spectral data. Alternatively, if the amount of light received is too low, the requisite level of detail may not be captured in the spectral signature.

SUMMARY

Aspects of the invention may include systems, methods and devices of the various embodiments that may enable dynamically calibrating intensity of a light source in a system for evaluating a skin lesion using Elastic-Scattering Spectroscopy (ESS). In an aspect of the invention, a method may include illuminating a sample of the skin lesion with a first pulse from the light source adjusted to a high output setting, receiving a signal including an elastic scattering spectrum resulting from illuminating the skin lesion sample at the high output setting, determining whether the received signal has an intensity greater than a saturation threshold associated with at least one optical detection sensor, and storing the elastic scattering spectrum resulting from illuminating the skin lesion sample at the high output setting in response to determining that the received signal has an intensity greater than the saturation threshold. In an aspect, the method may also include, in response to determining that the received signal does not have an intensity greater than the saturation threshold, illuminating the skin lesion sample with a second pulse from the light source adjusted to a low output setting, receiving a signal including an elastic scattering spectrum resulting from illuminating the skin lesion sample at the low output setting, and storing the elastic scattering spectrum resulting from illuminating the skin lesion sample at the low output setting.

In an aspect, the method may also include computing normalized spectral data for the lesion sample based on the stored elastic scattering spectrum and a reference sample signal. In an aspect, the reference sample signal may be an elastic scattering spectrum resulting from illuminating the reference sample with the light source adjusted to the same setting used to generate the stored elastic scattering spectrum.

In an aspect, the high output setting may be a maximum intensity capable of being produced by the light source. In aspects, the low output setting may be a level that is less than 25% of the maximum intensity capable of being produced by the light source.

In an aspect, the saturation threshold may include a preset intensity level based on capabilities of at least one optical detection sensor.

In an aspect, the saturation threshold may be 80% of the possible sensitivity of the at least one optical detection sensor.

In aspects, the light source may be at least one discrete narrow-band light source. In some embodiments, the at least one discrete narrow-band light source may include one or more light emitting diode (LED) or a laser diode.

In aspects, the reference sample may be a material that exhibits approximately Lambertian reflectance. In aspects, illuminating the skin lesion sample may include placing a fiber optic illumination source in contact with the skin lesion, wherein elastic scattering spectra are received through a fiber optic collector.

Further aspects may include generating an output based on the classification of the skin lesion, and sending the result of the comparison to a third-party medical provider. In other aspects, the method may further include performing image analysis on the skin lesion using at least one characteristic detection algorithm.

Further aspects may include a system for evaluating a skin lesion using Elastic-Scattering Spectroscopy (ESS) having a processor configured to perform one or more operations of any of the methods summarized above. Further aspects include system for evaluating a skin lesion using Elastic-Scattering Spectroscopy (ESS) having means for performing functions of any of the methods summarized above. Further aspects may include a non-transitory processor-readable storage medium having stored thereon processor-executable instructions configured to cause processor of a system for evaluating a skin lesion using Elastic-Scattering Spectroscopy (ESS) to perform operations of any of the methods summarized above.

BRIEF DESCRIPTION OF THE DRAWINGS

The accompanying drawings, which are incorporated herein and constitute part of this specification, illustrate exemplary embodiments of the invention, and together with the general description given and the detailed description, serve to explain the features herein.

DETAILED DESCRIPTION OF THE INVENTION

Any reference to claim elements in the singular, for example, using the articles "a," "an" or "the," is not to be construed as limiting the element to the singular. The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention.

The various embodiments may include systems, methods and devices for enabling improved detection of skin cancers by using a combination of image analysis and Elastic-Scattering Spectroscopy (ESS).

Optical spectroscopy techniques, including elastic-scattering spectroscopy (ESS), provide a minimally invasive approach for obtaining spectral measurements of the scattering properties of tissue. These techniques allow for the acquisition of spectral signatures of the underlying tissue, for the purpose screening for skin cancer. ESS is sensitive to the wavelength dependence of the tissue optical scattering properties, which vary due to architectural changes at the cellular and sub-cellular level as a result of different pathologies of the subject tissue under analysis.

In some embodiments, image analysis may be implemented in addition to using ESS. Image analysis may include visual analysis of lesions that include different characteristics indicative of skin cancer. Such characteristics may include, but are not limited to, asymmetry, border irregularity, non-uniformity of color, texture patterning, etc. In some embodiments, such analysis may be performed on various image types (e.g., confocal, dermoscopic, clinical, etc.). In some embodiments, additional analyses not based on imaging may be further implemented in combination with ESS and image analysis, such as genetic and/or other testing.

In various embodiments, image detection processes may be embedded in a user platform that includes, for example, determination of skin type, information on UV radiation, archiving of lesions. Such platform may be implemented using a smartphone or other portable imaging device. For example, a smartphone configured with sufficient capabilities (e.g., with at least an 8 megapixel autofocus camera) may be used to take multiple photographs of a lesion. An application installed on the smartphone may be used to perform fractal analysis or utilize one or more other algorithm.

The onset of skin cancer may bring about micro-morphological changes to cells in the basal layer of the epidermis. For example, in pigmented carcinomas (e.g., melanoma) such changes may be in the melanin, the melanocytes, and the melanosomes. Melanin and melanosomes have long been identified as significant optical scattering centers. In benign tissue, the melanosomes are ellipsoidal shaped with an even distribution of melanin macromolecules predominantly toward one end (as melanization occurs in the melanosome). The advent of malignant tumors, such as melanomas, may alter this morphology, changing the shape of the melanosome to something closer to spherical, granularizing the distribution of the melanin and changing the packing density, among other effects. Such skin cancers may also alter the molecular structure of the melanin itself.

In various embodiments, ESS may be employed to identify the changes in the size distribution and index of scattering of melanin to the onset of cancer in skin lesions. ESS (or diffuse-reflectance spectroscopy), is a point spectroscopic measurement technique that is capable of providing scattered light spectra with information about the microscopic properties occurring in superficial tissues at the cellular and sub-cellular level. Such properties may include, for example, sub-cellular morphology of tissue, nuclear size and density, hyperchromaticity, DNA condensation and chromatin granularity, nuclear crowding, and changes in the size/density of mitochondria and other cellular organelles or structural proteins. Specifically, variations in the optical refractive index (i.e., variations in density) of cellular structure cause light to scatter. While scattering occurs in random directions, the probability of scattering depends on the wavelength (color) of the light, and the sizes and densities of the particles. Thus, measurements of the relative intensity of scattered light at different wavelengths may be correlated with tissue disease status.

Examples of spectroscopy techniques that may be used to perform the optical detection of skin cancers in the various embodiments are described in U.S. Published Patent Application No. 2013/0253335 entitled "Optical Process and Apparatus for Non-Invasive Detection of Melanoma", U.S. Pat. No. 8,406,861 entitled "Detecting optical properties of a turbid medium", and U.S. Pat. No. 9,072,428 entitled "Classification techniques for medical diagnostics using optical spectroscopy", the contents of which are incorporated by reference herein.

In various embodiment, dynamic calibration may provide a method for optimizing the level of illumination for subsequent spectroscopy techniques, such as ESS. In various embodiments, ESS may be performed by sequentially delivering light within the wavelength range from near-ultraviolet (UV) to near-infrared (IR) (e.g., around 320-850 nm) through an illuminating fiber to a skin lesion. In an example, ESS may be carried out at a set of appropriately chosen individual wavelengths at which skin cancers (including melanoma and non-melanoma skin cancers) demonstrate unique spectral features as compared to other lesions. Light at each of the individual wavelengths may be delivered to the skin lesion through an illuminating fiber, and a portion of backscattered light may be collected through an adjacent fiber and conveyed to light-detection sensors in a control system. The collected backscattered light may be evaluated based on the intensity of the scattering at each wavelength may be identified. In other words, changes in the scattering as a function of the different wavelengths due to the optical index gradients of cellular and sub-cellular structures may enable automated classification of the lesion as likely benign or malignant.

ESS may be performed using a system configured with a lighting system (i.e., an illumination device and an acquisition system that can capture the optical signal from lesions at discrete wavelengths), and a processor. For example, an ESS system may been designed to include pulsed bright light emitting diodes (LEDs), a probe made of separate illuminating and collecting fibers (e.g., 200 nm in diameter) that are placed in optical contact with the lesion, a microcontroller board, and power supply.

In various embodiments the system may include a memory configured with processor-executable instructions that constitute ESS software/application for performing data analysis and comparisons of spectral signatures. In some embodiments, the memory configured with the ESS software may be provided as part of a smartphone to which the lighting and acquisition systems may connect or interface.

The overall intensity of the backscattered signal (i.e., portion of collected backscattered light) delivered to the optical detection sensor(s) depends on the level of absorption of the sample tissue (i.e., skin sample) and the amount of light delivered to the tissue. That is, the absorption of the sample tissue determines what portion of an original light pulse may be reflected in the scattering spectrum and collected as backscattered light. Such absorption may vary, for example, based on lesion pigmentation.

Depending on the particular tissue sample, the intensity of the backscattered signal may be too high or too low for the capabilities of the optical detection sensor(s). In instances in which the delivered light intensity is too high, the signal may be cut-off. In contrast, in instances in which the delivered light intensity is too low, the spectral details that enable discrimination between lesion types may be degraded.

Therefore, the various embodiments may enable calibration of the intensity of the light delivered by the illumination component (e.g., fiber) to account for the sensitivity of the optical detection sensor(s) in the ESS system. Specifically, in various embodiments, the intensity of the light source may be adjusted based on the absorption of the tissue sample, thereby optimizing quality of the spectral data obtained for a sample.

In various embodiments, the light emitting component of the ESS system may be associated with a controller that has a calculated range to enable changes to the output. Such controller may allow linear adjustments as a percentage of the total output capability. Additionally or alternatively, the controller may allow for non-linear adjustments of the output. In various embodiments, the calibration process may be suitable for use in any of a variety of devices and systems, each of which may define an optimal return signal (i.e., amount of collected backscattered light), and optionally a tolerance range (e.g., +/−5%).

In various embodiments, the controller may be adjusted initially for delivery of a maximum light output. The delivery component of the lighting system (e.g., a probe of an illumination optical fiber) may be placed over a tissue sample, and may deliver a single light pulse at the maximum amount. If the amount of backscattered light is lower than or within the tolerance range of an optimal return signal, the maximum amount setting may be stored as the preferred intensity setting for the sample. If the amount of backscattered light is greater than the tolerance range of the optimal return signal, the controller may be adjusted to a lower light output, and the lighting system may deliver another single pulse. In some embodiments, the lower light output may be the minimum output level for the lighting system. In other embodiments, the lower light output may be, for example, a setting that is 0-25% of the maximum light output for the lighting system. The controller may store the lower light output level as the preferred intensity for the sample.

In some embodiments, if the illumination source is able to pulse light fast enough and has a relatively large range of output, the process of calibration may involve a number of repeated iterations. For example, if the return signal from pulsing the sample at the lower light output setting is below the tolerance range of the optimal return signal, the controller may be adjusted to a level that is between the maximum output and the last output. These adjustments and delivery of a light pulse may be repeated until the amount of backscattered light is within the tolerance range of the optimal return signal, or alternatively, to get as close as possible within a pre-selected number of attempts (e.g., 3-5). Once reached, the controller may store the last light output level as the preferred intensity setting for the light source for the sample.

While the various embodiments are described in connection with ESS for the purpose of identifying changes indicative of skin cancer, they are not limited to such use. That is, the methods of dynamic calibration according to various embodiments may be employed for any of a number of other types of spectroscopy in which a sample material may have varying absorption/reflection properties.

Figure 1:
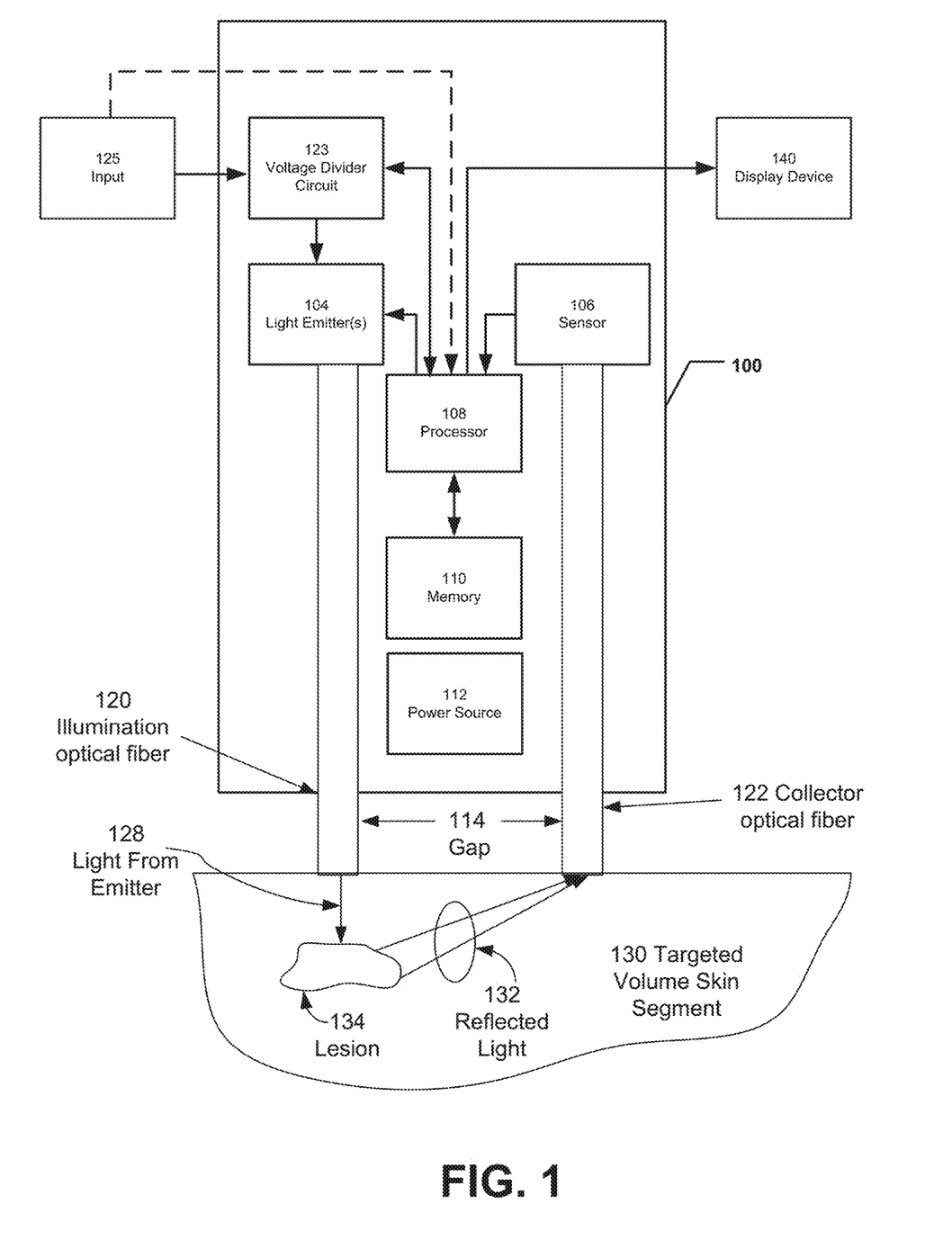
FIG. 1 is a block diagram illustrating a lighting system for performing elastic scattering spectroscopy (ESS) according to various embodiments.

FIG. 1 shows an example lighting system 100 that may be part of an ESS system. A processor 108 in the lighting system 100 may execute instructions stored in the memory 110 to initiate a sequence of illuminations. By way of illustration and not by way of limitation, the processor 108 may be responsive to a "start" button (not illustrated) that runs through a preselected illuminations using the light emitters from one or more light emitter 104. A user may be signaled when the lighting system 100 should be moved. After the device 100 is properly positioned, the user may depress the start button again and the sequence of illuminations repeats.

In an embodiment the light 128 may be passed through the illumination optical fiber 120 to a termination point that is placed upon the subject lesion 134. The light 128 delivered from the fiber 120 may be directed onto lesion 134, where it may interact with the melanin molecules in the lesion 134. A fraction of the scattered/reflected light 132 may be returned toward the surface of the targeted volume of skin segment 130. The collector optical fiber 122 may be positioned next to the delivered light source separated by some distance gap 114. The collector optical fiber 122 may collect some of the light scattered (i.e., reflected) from the melanin molecules. The collector optical fiber 122 carries the collected light back to a sensor 106, which may detect the intensity of the reflected light. By way of illustration and not by way of limitation, the sensor 106 be an avalanche photo diode.

In some embodiments, the light emitter(s) 104 may include at least one discrete narrow-band light source (e.g., LED or laser diode). In some embodiments, the light emitter(s) 104 may include at least one broadband light source (e.g., xenon arc lamp or broadband LED).

In various embodiments, the processor 108 may be coupled to a voltage divider circuit 123 that powers the illumination source (i.e., light emitter(s) 104) to create a desired level of brightness. Specifically, instructions executed by the processor 108 may include a desired output level that is passed to the voltage divider circuit 123, which increases or decreases the resistance applied to the power to the illumination source. In various embodiments, the voltage divider circuit may output a voltage that varies within a set range (e.g., 0V to 3.3V). The voltage may be read by the processor to appropriately scale the brightness level. For example, a 3.3V signal would represent 100% light output, while a 1.65V signal would represent 50% light output.

In various embodiments, the voltage divider circuit 123 may be an analog or digital potentiometer. In various embodiments, the potentiometer may change its resistance value according to the position of an adjustable dial or other input 125 may be set by a user. In some embodiments, the resistance value may be selected based on prior use of the device to sample a lesion which may have a similar level of pigmentation, or by sampling a baseline of skin that is known to be normal/lesion-free.

In an embodiment, the processor 108 may execute instructions included in memory 110 to determine whether the reflected light 132 is indicative of the potential presence of skin cancer. For example, the processor 308 may output a resulting classification to a display device 140 indicating a likely presence or absence of skin cancer. Alternatively, the processor 108 may provide numeric values to the display device 140 so that the progression of a particular lesion may be assessed by the individual user or the medical professional. The numerical data may be stored in memory 110. In yet another embodiment, the display device 140 may be a computing device, such as, for example, a laptop computer, a desktop computer, a smartphone, etc. The display device 140 may provide additional functionality to the lighting system 100. For example, the processor 108 may communicate measurement data to the display device 140 which may then communicate the data to a medical professional over a network, such as for example and without limitation the Internet. In an embodiment, a user may send a number of readings over an extended period of time to a medical professional so that a diagnostic can be run each time a value is received. If these values indicate a trend within a particular confidence level, a warning may be sent to the medical professional and to the user of the device directing the user to seek additional or immediate medical attention for the lesion being evaluated.

As indicated above, the sensor 106 may detect the intensity of light scattered (i.e., reflected) by the lesion 134 under analysis. In an embodiment, the optical detection is done with a traditional heavily amplified photodiode combined with an analog-to-digital converter (ADC) to allow the analog photodiode to communicate with a digital microcontroller. It is the output signal of the ADC on which the on-board integrated circuits with the programmed analysis algorithms operate. Depending on the activation of the LEDs, the ADC output represents one of the aforementioned spectral analysis categories (individual intensity, slope, or integrated intensity).

In alternative embodiments, the traditional ADC may be replaced by an alternative digitizing system. Voltage to Frequency Converters and Current to Frequency Converters (VFC and CFC) has been a mainstay of digital electronics design for many years. By adding a photodiode to the input of a CFC, a "digital" photodetector with a large dynamic range is produced. These detectors—capable of monitoring light levels from several thousand LUX (sunny day) to as low as 20 LUX (very dark room)—are fast becoming a mainstay in the medical device community (in pulse oximeters, for example). The digital output may be easily interfaced to microcontrollers or signal processors. As the frequency of pulse output is proportional to the incident flux of light data collection is as simple as counting the number of pulses within a fixed time period, or to maintain accuracy the time interval can be dynamic. Pulses may be counted until a certain number is reached and the time interval is computed, this allows for a minimum noise threshold to be set but the application must not be time sensitive. Still another variation on this embodiment disclosed herein is to make the detector a traditional pixelated detector, such as a charge coupled device (CCD). This is used as a direct analog-to-digital converter. All of the light falling on every pixel of the CCD in this variation is summed in CCD control software, and that signal sent to the on-board integrated circuits for analysis with the melanoma detection algorithms.

The processor 108 may be of one or more memory-integrated circuit (MICs). These circuits may be capable of performing the functions of the standard digital integrated circuits, but can also store data and retrieve it, allowing for more complex calculations. This increases the flexibility in implementing the spectral analysis algorithm prescribed to detect the presence of skin cancer. Multiple-stage processes involving the use of the output of one circuit as input for another can be realized using MICs as the on-board processors.

In an embodiment, the lighting system 100 may be configured as a smart phone add-on detector that connects directly to a smart phone via a USB port or other pin connector, or a wireless connection (e.g., WiFi, Bluetooth, etc.). The detector may have its own internal power via a battery that is replaceable or rechargeable. This power source provides power for the light source. Alternatively, the add-on detector may be powered by the internal power source of the smart phone. The add-on detector comprises fiber-optic probes for delivery of the illumination to the lesion. In an embodiment, the add-on detector is rigidly connected to the smart phone such that the smart phone is brought in intimate contact with the lesion to be analyzed. The sample scattered light can then be collected via the rigidly connected add-on detector. Alternatively, the probe can be flexibly connected to an add-on detector unit such that the probe may be placed appropriately to sample a lesion without the need for maneuvering the entire smart phone device. The add-on detector interacts with an application on the smartphone, which may be the same or separate from an application on the smartphone that performs the image analysis.

In some embodiments, a single device may be used to implement both the image analysis and ESS. In some embodiments, a system may be designed that enables ESS and image analysis to be performed using separate devices that interface with one another (or with a third device) to combine the data and generate results (e.g., a classification of a lesion as benign or malignant). In embodiments in which the lighting system of an ESS system is configured as an add-on to a smartphone, the smartphone may be configured to capture the images and perform processing for image analysis. While discussed in the context of spectroscopy, the dynamic calibration in various embodiments may also enable calibration of the intensity of the light delivered by the illumination component for capturing image data for analysis.

Figure 2:
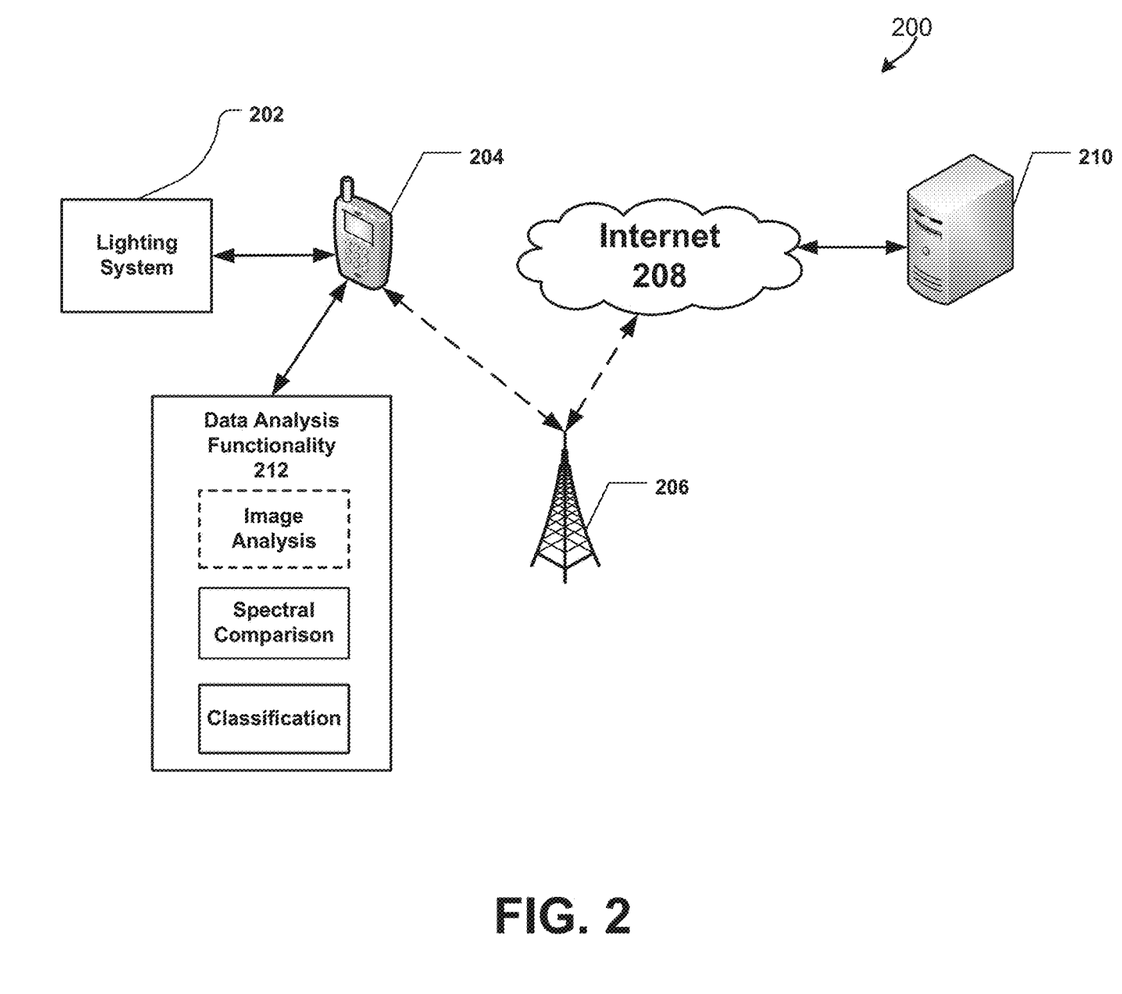
FIG. 2 illustrates a block diagram of a system suitable for use with various embodiments.

FIG. 2 illustrates an embodiment system 200 for performing ESS and, optionally, image analysis. With reference to FIGS. 1-2, an application may be downloaded to a user's wireless communication device 204 (e.g., a smartphone). In various embodiments, the application may have software instructions that may cause the to manage the operations of the lighting system shown in FIG. 1, and to receive spectral results from illumination of a lesion to the processor of the device 204.

Spectral comparison, and classification of the lesion may be part of data analysis functionality 212 provided by an application that may be stored on the device 204. The lighting system 202, which may be removably connected to device 204, may send results to the device 204 to be analyzed and reported using a display capability of the device 204.

In some embodiments, the data analysis functionality 212 may also include image analysis. In such embodiments, the image analysis may be performed prior to ESS, and may provide an initial risk assessment of a lesion. That is, a first level analysis may use image analysis to determine whether the risk of malignancy is sufficiently low to terminate analysis. If such risk is not low enough, a second level of analysis may use ESS and image analysis to attempt to classify the lesion. In this manner, unnecessary testing and false positives may be avoided, improving the efficiency of the system. In some embodiments, algorithms for combining ESS measurements and image analysis may be developed based on known models and/or machine learning over time.

In an embodiment, the communication capability of the device 204 may be programmed to automatically report the results over a wireless network 206 (e.g., a cellular network) connected to the Internet 208 and to a health care provider server 210. When results are reported, the healthcare provider may automatically schedule a follow-up meeting for the user in the event that the skin lesion is classified as potentially malignant.

Figure 3:
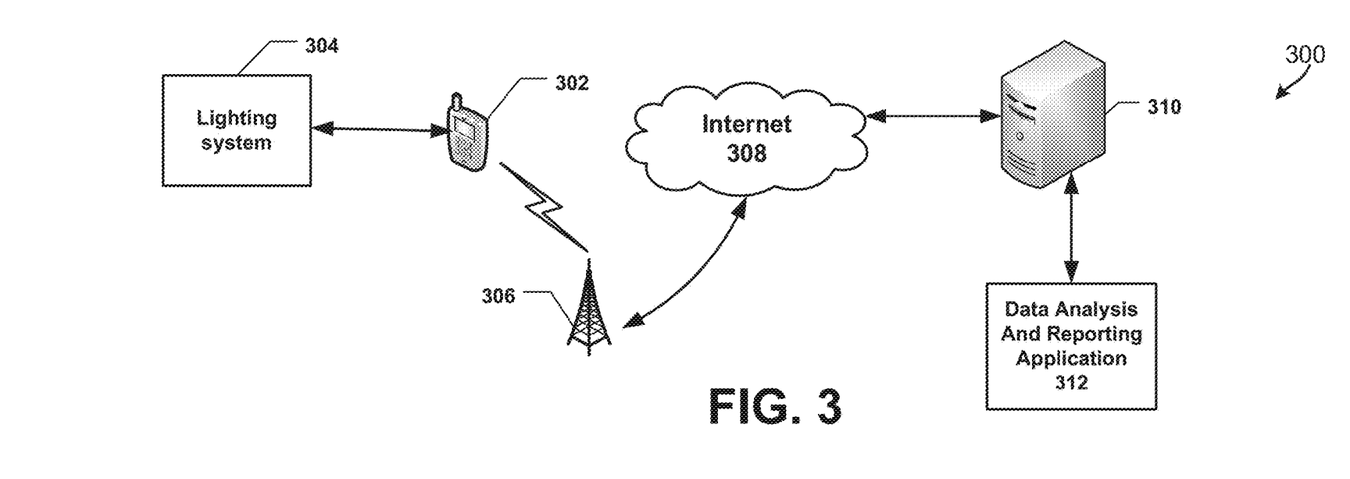
FIG. 3 illustrates a block diagram of a system suitable for use with various embodiments.

FIG. 3 illustrates another embodiment system 300 for performing ESS and, optionally, image analysis. With reference to FIGS. 1-3, a wireless device 302 (e.g., device 204) may be connected to a lighting system 304 (e.g., 202). The lighting system 304 may include the appropriate illumination sources (e.g., 120) and probes (e.g., 122) to illuminate a lesion and received the reflected light. A software application may be installed on the wireless device 302 that actuates the lighting system 304 to illuminate a lesion sample and record information for storage on the wireless device 302 (e.g., spectral data and/or images).

The wireless device 302 may communicate the spectral data and/or image data captured by the lighting system 304 over a wireless network 306 (e.g., a cellular network) connected to the Internet 308 and to a processor of a server 310.

In some embodiments, the server 310 may have stored instructions that cause the processor 310 to analyze the spectral data and/or image data transmitted from the wireless device 302. In some embodiments, data may be processed on the server 310, and results determined and transmitted back to the wireless device 302 to inform a user. In some embodiments, such functions may be performed by a data analysis and reporting application 312 stored on the processor.

Reporting of results may be immediate, or may be stored so that a physician can review the results prior to transmitting those results over the wireless network 306.

Figure 4:
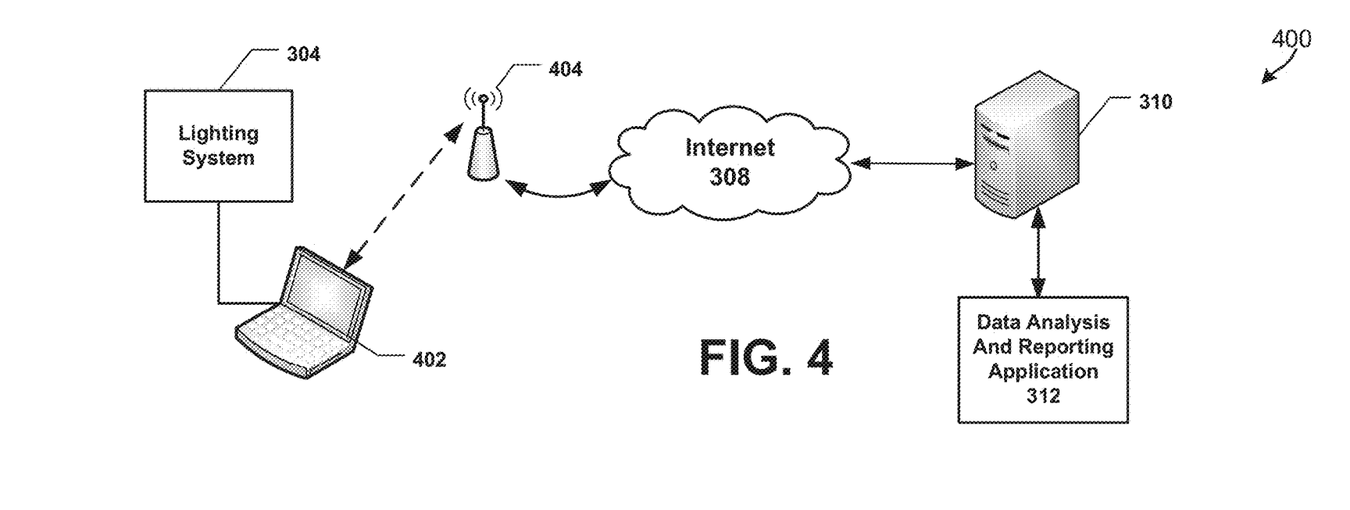
FIG. 4 illustrates a block diagram of a system suitable for use with various embodiments.

FIG. 4 illustrates another embodiment system 400 for performing ESS and, optionally, image analysis. With reference to FIGS. 1-4, in system 400 the lighting system 304 may be connected to a computing device 402. In various embodiments, the computing device 402 may be connected to the Internet 308 via an access point 404. In this manner, the computing device 402 may communicate the results of the spectral detection and/or image analysis to the processor of the server 310.

In various embodiments, the server 310 may have stored instructions that cause the processor to analyze the spectral data and/or images received from the computing device 402. In some embodiments, data may be processed on the server 310, and results determined and transmitted back to the computing device 402. In some embodiments, these instructions may be provided through the data analysis and reporting application 312 stored on the processor.

Figure 5:
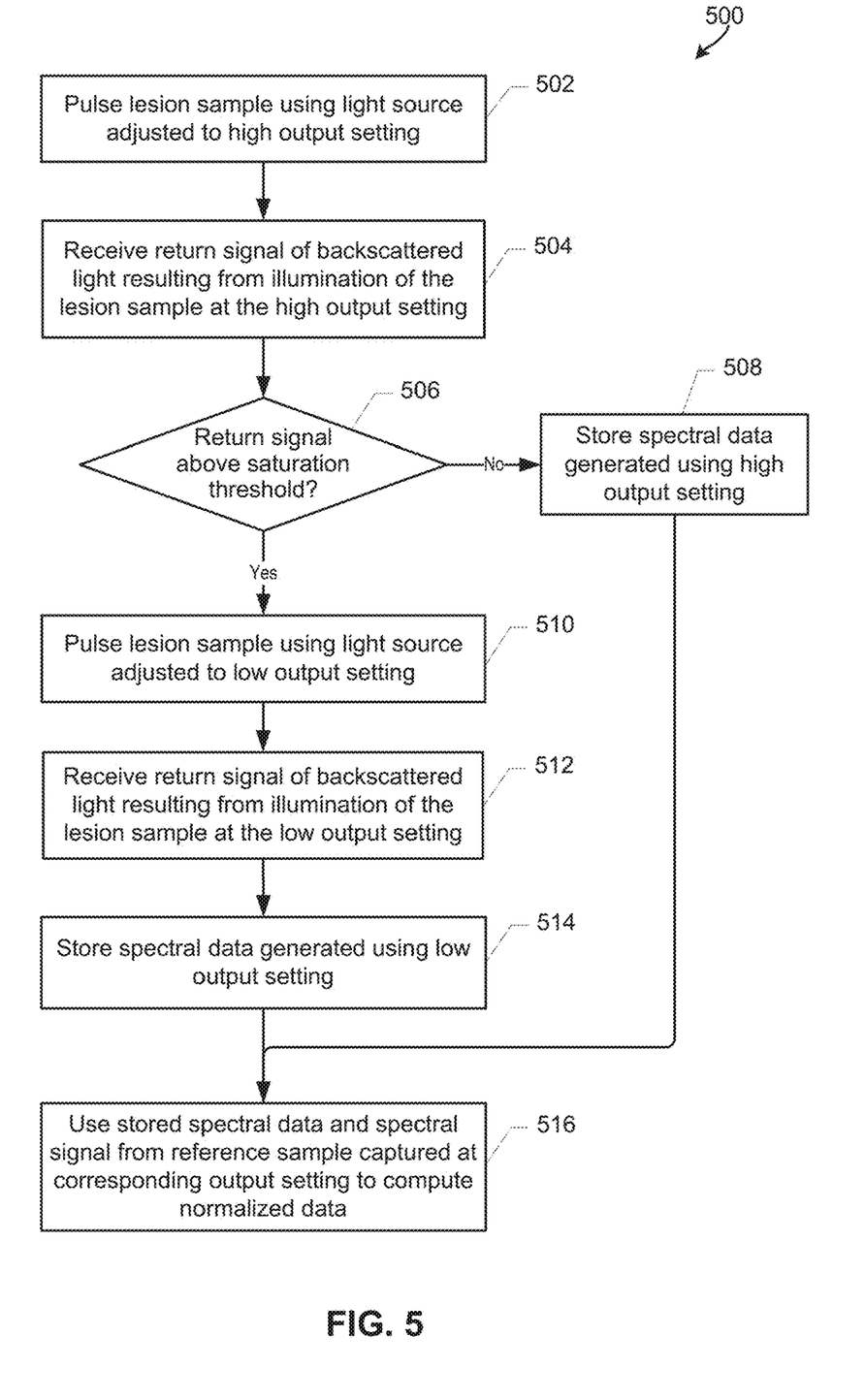
FIG. 5 is a process flow diagram illustrating a method for calibrating intensity of a light source in a spectroscopy system suitable for use with various embodiments.

FIG. 5 illustrates a method 500 for dynamically calibrating the intensity of the light source in an ESS system based on the capabilities of the detection sensor according to some embodiments. With reference to FIGS. 1-5, in various embodiments, the operations of method 500 may be implemented by one or more controller that includes components of a lighting system (e.g., 100, 202, 304), such as a processor (e.g., 108, 210, 310), a sensor (e.g., 106), and/or a voltage divider circuit (e.g., 123). In various embodiments, the operations of the method 500 may be implemented by a separate controller (not shown) that may be coupled to a processor (e.g., 108, 210, 310), a sensor (e.g., 106), and/or to a voltage divider circuit (e.g., 123).

In block 502, the lighting system controller may pulse a lesion sample in a tissue under examination with the light source adjusted to a high output setting. For example, the high output setting in various embodiments may correspond to a maximum intensity of the light source (e.g., light emitters 104). In some embodiments, the light source may be adjusted to the high output setting automatically, such as in response to starting a calibration protocol. In other embodiments, the light source may be adjusted to the high output setting manually through user input selecting such setting.

In block 504, the lighting system controller may receive a return signal comprising backscattered light resulting from the illumination of the lesion sample at the high output setting. In various embodiments, the backscattered light (e.g., elastic scattering spectrum) may be collected by components of the lighting system such as an optical fiber (e.g., 122), and provided to the sensor.

In determination block 506, the lighting system controller may determine whether the return signal is above a saturation threshold. In various embodiments, the saturation threshold may be a preset intensity level that is based on capabilities of the sensor of the lighting system, and may include a tolerance range.

For example, if the saturation threshold for a sensor is 80% of the possible sensitivity of the sensor with a tolerance range of +/−5%, the saturation threshold may be configured as 85%. Such values are provided merely as examples, as the saturation level and/or tolerance range may be any percentage depending on the equipment used.

In embodiments using a broadband light source, determining whether the return signal is above the saturation threshold may involve determining whether the largest peak of the return signal is clipped, despite other peaks that may be within an acceptable range.

In response to determining that the return signal is not above the saturation threshold (e.g., determination block 506="No"), the lighting system controller may store the spectral data generated using the high output setting—that is, the return signal received in block 504. The spectral data (e.g., elastic scattering spectrum) may be stored in memory coupled to a processor of the system.

In response to determining that the return signal is above the saturation threshold (e.g., determination block 506="Yes"), the lighting system controller may pulse the lesion sample with the light source adjusted to a low output setting in block 510. For example, the low output setting in various embodiments may correspond to a minimum intensity of the light source (e.g., 0% intensity), or to a preselected level below a percentage of the maximum intensity (e.g., less than 25%). In some embodiments, the lighting system controller may automatically change the light source to the low output setting. In other embodiments, the light source may be adjusted to the low output setting manually by the user based on output by the lighting system. Such output may be, for example, an instruction or indication on a display (e.g., 140), an audio output, etc. In other embodiments, the lighting system controller may output a result indicating that the sample is not acceptable because it cannot be accommodated by the capabilities of the lighting source and produces invalid results (not shown).

In block 512, the lighting system controller may receive a return signal comprising backscattered light resulting from the illumination of the lesion sample at the low output setting. In block 514, the lighting system controller may store the spectral data generated using the low output setting (i.e., the return signal received in block 512). In block 516, the lighting system controller may use the stored spectral data and spectral data from a reference sample captured at a corresponding output to compute normalized data.

For example, if the stored spectral data for the lesion sample was generated using the high output setting, the comparison may be to spectral data generated by pulsing a reference sample with the light source adjusted to the high output setting. Alternatively, if the stored spectral data for the lesion sample was generated using the low output setting, the comparison may be to spectral data generated by pulsing a reference sample with the light source adjusted to the low output setting.

In some embodiments, spectral data for the reference sample may be captured either before or after the calibration of the source light intensity. For example, in some embodiments, spectral data from the reference sample at both the high and low output settings of the light source may be collected in advance of performing the method 500. In other embodiments, spectral data from the reference sample may be generated after spectral data from the lesion sample is stored using the last illumination setting for which a return signal was received. In various embodiments, the reference sample may be a material that exhibits Lambertian reflectance—that is, true reflection of diffusion with constant radiance in all directions. A reflecting Lambertian surface may provide perfectly diffuse scattering (i.e., maintaining wavelength and intensity) that is fully independent of the direction of the incoming light source, rendering the reflectance completely proportional to the total radiant power reaching the surface.

In some embodiments, the normalized spectral data may be computed using backscattered light collected at a plurality of different wavelength for each lesion sample.

Figure 6A:
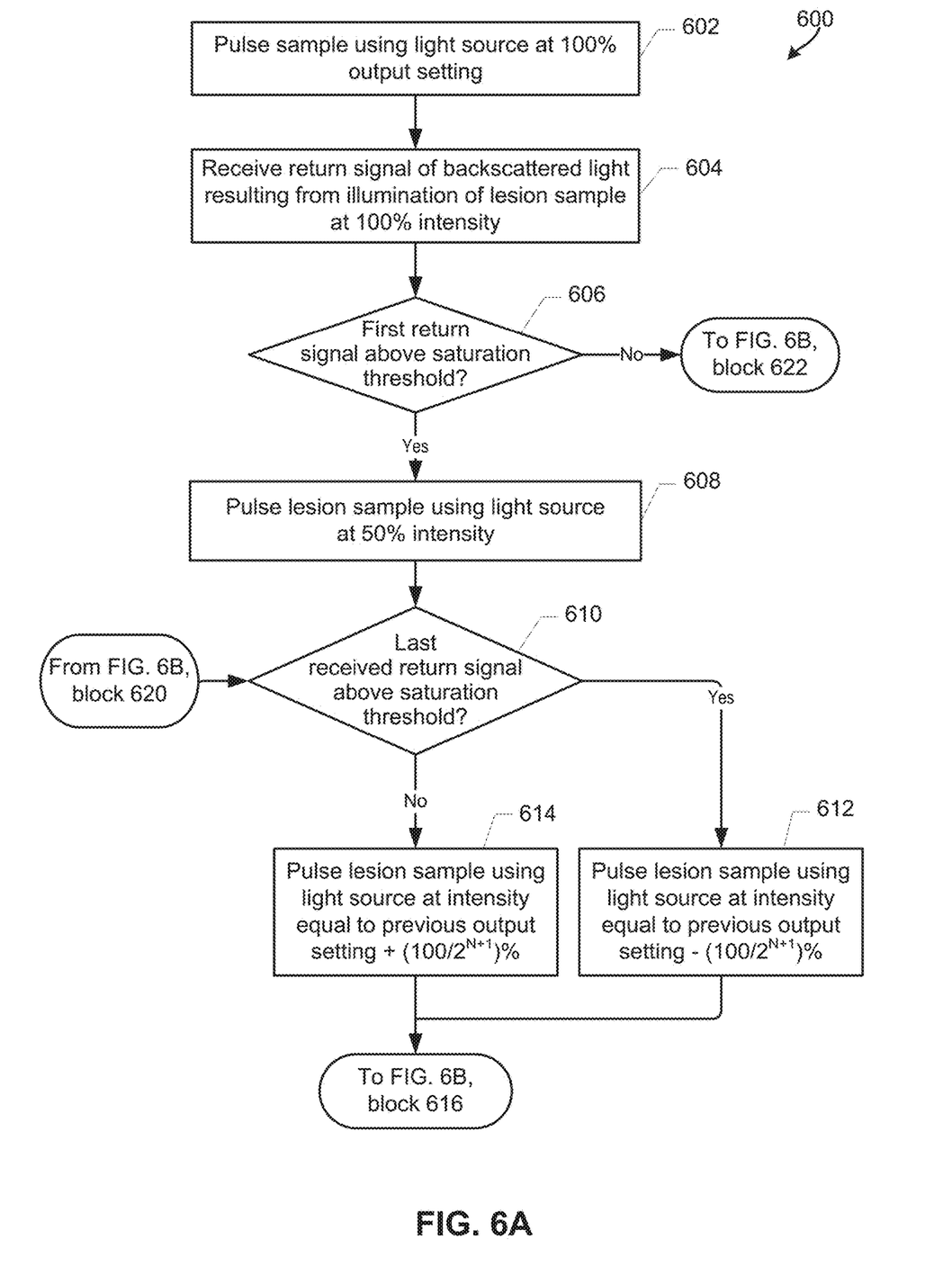
FIGS. 6A-6B are process flow diagrams illustrating a method for calibrating intensity of a light source in a spectroscopy system suitable for use with various embodiments.
Figure 6B:
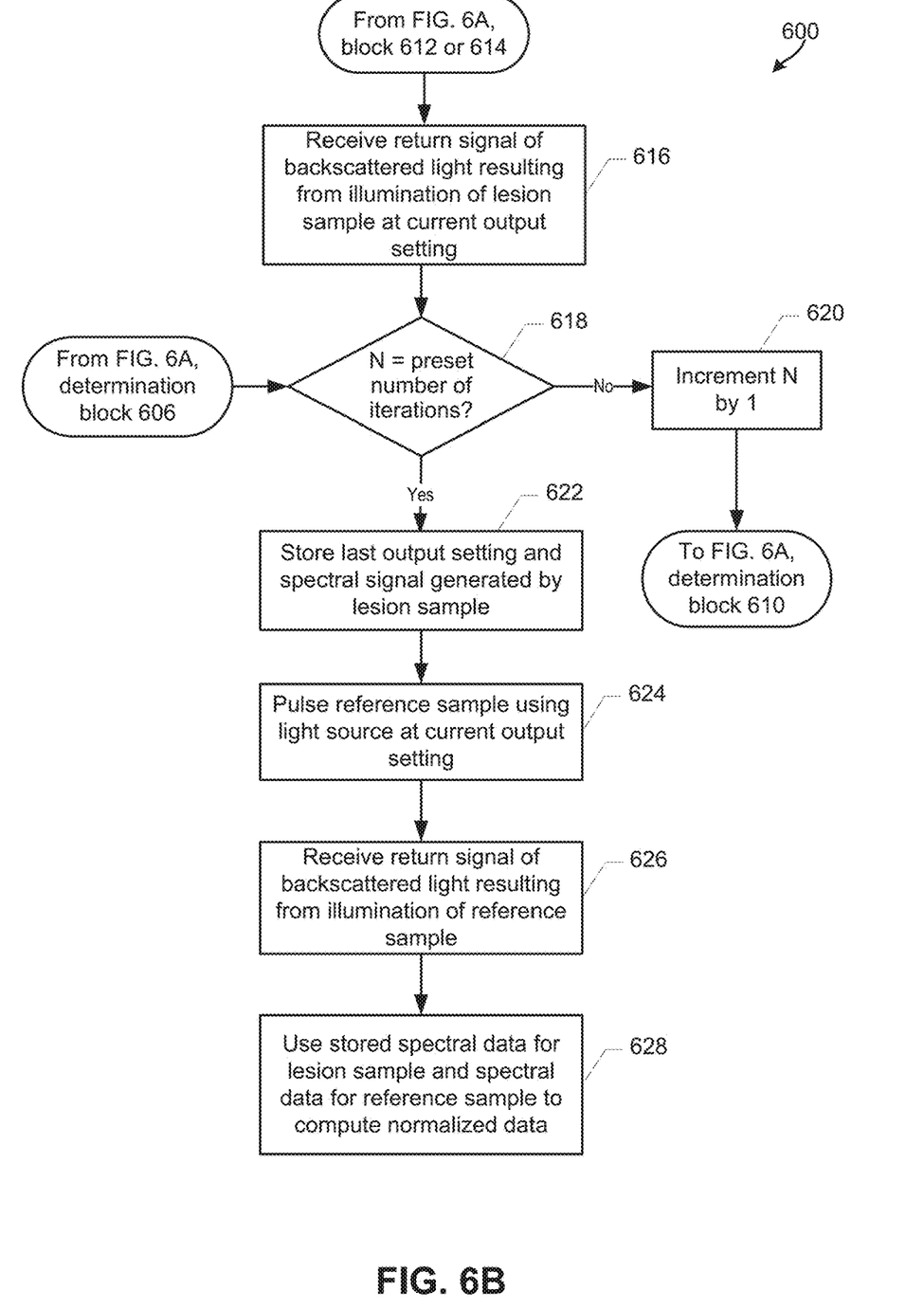

Depending on the properties of the ESS system, calibration of the light source intensity in an ESS system may involve using more than two possible output settings, instead going through a number of repeated iterations to identify a preferred intensity output. An example of such calibration is shown in FIGS. 6A-6B, which illustrates method 600 as an alternative for dynamically calibrating the intensity of the light source in an ESS system based on the capabilities of the detection sensor. In various embodiments, calibration using method 600 may be preferred if the illumination source is able to pulse light relatively quickly, and/or if the illumination source has a large range of possible intensities.

With reference to FIGS. 1-6B, in various embodiments, the operations of method 600 may be implemented by one or more controller that includes components of a lighting system (e.g., 100, 202, 304), such as a processor (e.g., 108, 210, 310), a sensor (e.g., 106), and/or a voltage divider circuit (e.g., 123). In various embodiments, the operations of the method 600 may be implemented by a separate controller (not shown) that may be coupled to a processor (e.g., 108), a sensor (e.g., 106), and/or to a voltage divider circuit (e.g., 123).

In block 602, the lighting system controller may pulse a lesion sample in a tissue under examination with the light source adjusted to a maximum output setting (i.e., 100% intensity). In some embodiments, the light source (e.g., 104) may be adjusted to the maximum output setting automatically, such as in response to starting a calibration protocol. In other embodiments, the light source may be adjusted to the maximum output setting manually through user input selecting such setting.

In block 604, the lighting system controller may receive a return signal comprising backscattered light resulting from illumination of the lesion sample at the maximum output setting. In various embodiments, the backscattered light may be collected by components of the lighting system such as an optical fiber (e.g., 122), and provided to the sensor (e.g., 106).

In determination block 606, the lighting system controller may determine whether the first return signal is above a saturation threshold. In various embodiments, the saturation threshold may be a preset intensity level that is based on capabilities of the sensor of the lighting system, such as 80% of the possible sensitivity of the sensor. In response to determining that the first return signal is above the saturation threshold (e.g., determination block 606="Yes"), the lighting system controller may pulse the lesion sample with the light source adjusted to a 50% intensity setting in block 608.

In some embodiments, a present number of calibration cycles (i.e., iterations) may be established for the ESS system. The default number may be configured, for example, based on the output range and levels of the light source, the sensitivity of the optical detector (i.e., sensor), and the requisite level of detail in the resulting spectral data considering the amount of time practically allocated for calibration. In some embodiments, the preset number of iterations may be configured by an operator. For example, the preset number of iterations may be set in the range of 2-5. In various embodiments, a cycle count "N" may be initially set to a value of 1, and used to keep track of the iterations during the calibration process.

In determination block 610, the lighting system controller may determine whether the last received return signal is above the saturation threshold. In response to determining that the last received return signal is above the saturation threshold (e.g., determination block 610="Yes"), the lighting system controller may pulse the lesion sample with the light source adjusted to a reduced intensity setting in block 612. In various embodiments, the reduced intensity setting may be computed as according to Equation 1:

$$\text{Reduced intensity setting} = \text{previous setting} - \left(\frac{100}{2^{N+1}}\right)\%. \quad \text{Eq. 1}$$

For example, during the first cycle (N=1) and with a previous setting of 50% intensity, the reduced intensity setting may equal 25% intensity (i.e., 50%–(100;4)%). In response to determining that the last received return signal is not above the saturation threshold (e.g., determination block 610="No"), the lighting system controller may pulse the lesion sample with the light source adjusted to an increased intensity setting in block 614. In various embodiments, the increased intensity setting may be computed as according to Equation 2:

$$\text{Increased intensity setting} = \text{previous setting} + \left(\frac{100}{2^{N+1}}\right)\%. \quad \text{Eq. 2}$$

For example, during the first cycle (N=1), with a previous setting of 50%, the increased intensity setting may equal 75% (i.e., 50%+(100;4)%).

In block 616, the lighting system controller may receive a return signal comprising backscattered light resulting from illumination of the lesion sample at the current output setting. In various embodiments, the current output setting may be a reduced intensity setting from block 612, or may be an increased intensity setting from block 614. In various embodiments, the backscattered light may be collected by components of the lighting system such as an optical fiber (e.g., 122), and provided to the sensor (e.g., 106).

In determination block 618, the lighting system controller may determine whether the value of N is equal to the preset number of iterations. In response to determining that the value of N is not equal to the preset number of iterations (i.e., determination block 618="No"), the lighting system controller may increment the value of N by 1 in block 620, returning to determination block 610. the steps of determination block 610 through block 616 may be repeated until the cycle count reaches the preset number of iterations.

As an example, if the last received return signal in the second pass (i.e., N=2) of determination block 610 was generated at 25% intensity, if such signal is not above the saturation threshold the lighting system controller may pulse the lesion sample at an increased intensity setting that equals 37.5% in block 614 (i.e., 25%+(100;8)%).

In response to determining that the value of N is equal to the preset number of iterations (e.g., determination block 616="No"), or in response to determining that the first return signal is not above the saturation threshold (e.g., determination block 606="No"), the lighting system controller may store the current light output setting and the spectral data generated using the current output setting in block 622. In various embodiments, the current output setting may be a percentage of the output capability of the light source.

In block 624, the lighting system controller may pulse a reference sample with the light source adjusted to the current output setting. In block 626, the lighting system controller may receive a return signal comprising backscattered light resulting from illumination of the reference sample at the current output setting.

In block 628, the lighting system controller may use the stored spectral data and the received spectral data for the reference sample to compute normalized data. For example, if the stored spectral data for the lesion sample was generated at a 100% intensity setting, the normalized data may be computed using spectral data generated by pulsing the reference sample with the light source adjusted to 100% intensity.

For the various adjustments of the light output in method 600, the lighting system controller may automatically change the light source to the next output setting, while in other embodiments the light source may be adjusted to the next output setting manually by the user in response to a display or other indicator with instructions.

In some embodiments, dynamic calibration according to method 500 and/or method 600 may be performed for multiple sample points on a single skin lesion. In some embodiments, for each sample to be acquired on a suspected skin lesion, the ESS system may identify and record the calibrated light output setting a for each sample point, in addition to storing the received spectral data. Once spectral data for the multiple sample points is completed, the light source may be placed within proximity of the reference material. The lighting system controller may pulse the reference sample at each recorded calibrated light output setting. In this manner, the ESS system may generate, for each point on the suspected lesion, a pair of signals—that is, the spectral data captured from the lesion point, and a corresponding reference.

Figure 7:
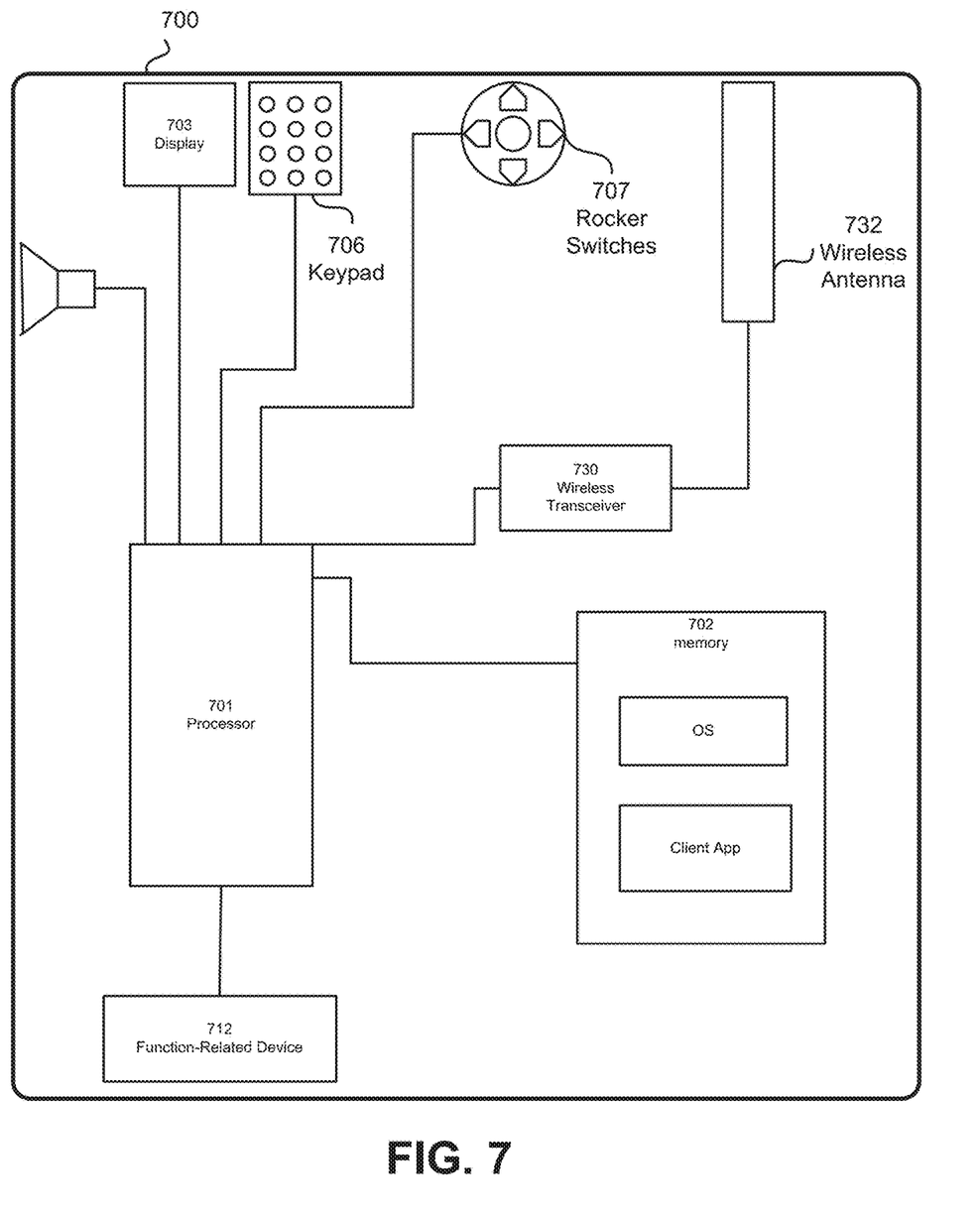
FIG. 7 illustrates a component diagram of an example wireless communication device suitable for use with various embodiments.

FIG. 7 illustrates a wireless communication device suitable for use in various embodiments. With reference to FIGS. 1-7, the wireless communication device 700 may be a smartphone, tablet, or other computing device (e.g., 204, 302, 402). In various embodiments, the wireless communication device 700 may include a processor 701 coupled to an internal memory 702 and to a display 703. Wireless devices typically also include a key pad 706 or miniature keyboard and menu selection buttons or rocker switches 707 for receiving user inputs. A wireless transceiver 330 may be coupled to the processor 701 and an antenna 732 for communicating wirelessly with another device. By way of illustration and not by way of limitation, the wireless transceiver may be compliant with Zigbee standards.

In various embodiments, a function-related device 712 may also be coupled to the processor 701. For example, if the wireless communication device 700 is intended to operate as a printer, the function-related device 712 may be a print engine. The processor 701 may be any programmable microprocessor, microcomputer or multiple processor chip or chips that can be configured by software instructions (applications) to perform a variety of functions, including the functions of the various embodiments described herein. In some wireless communication devices 700, multiple processors 701 may be provided, such as one processor dedicated to wireless communication functions and one processor dedicated to running other applications. Typically, software applications may be stored in the internal memory 702 before they are accessed and loaded into the processor 701.

In some wireless communication devices 700, the processor 701 may include internal memory sufficient to store the application software instructions. As part of the processor, such a secure memory may not be replaced or accessed without damaging or replacing the processor. In many wireless devices, the internal memory 702 may be a volatile or nonvolatile memory, such as flash memory, or a mixture of both. For the purposes of this description, a general reference to memory refers to all memory accessible by the processor 701, including internal memory 702, removable memory plugged into the wireless device, and memory within the processor 701 itself, including the secure memory.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein.

A general-purpose processor may be a microprocessor, but, in the alternative, the processor may be any conventional processor, controller, microcontroller, or state machine. A processor may also be implemented as a combination of wireless devices, e.g., a combination of a DSP and a microprocessor, a plurality of microprocessors, one or more microprocessors in conjunction with a DSP core, or any other such configuration. Alternatively, some blocks or methods may be performed by circuitry that is specific to a given function. In one or more exemplary aspects, the functions described may be implemented in hardware, software, firmware, or any combination thereof. If implemented in software, the functions may be stored on or transmitted over as one or more instructions or code on a computer-readable medium. The blocks of a method or algorithm disclosed herein may be embodied in a processor-executable software module, which may reside on a computer-readable medium. Computer-readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

What is claimed is:

1. A method for calibrating intensity of a light source in a system for evaluating a skin lesion using Elastic-Scattering Spectroscopy (ESS), the method comprising:
    illuminating a sample of the skin lesion with a first pulse from the light source adjusted to a high output setting;
    receiving a signal comprising an elastic scattering spectrum resulting from illuminating the sample of the skin lesion at the high output setting;
    determining whether the received signal has an intensity that is greater than a saturation threshold associated with at least one optical detection sensor;
    storing the elastic scattering spectrum resulting from illuminating the sample of the skin lesion at the high output setting in response to determining that the received signal has an intensity greater than the saturation threshold; and
    in response to determining that the received signal does not have an intensity greater than the saturation threshold:
        illuminating the sample of the skin lesion with a second pulse from the light source adjusted to a low output setting;
        receiving a signal comprising an elastic scattering spectrum resulting from illuminating the sample of the skin lesion at the low output setting; and
        storing the elastic scattering spectrum resulting from illuminating the sample of the skin lesion at the low output setting; and
    computing normalized spectral data for the skin lesion based on the stored elastic scattering spectrum and a reference sample signal.

2. The method of claim 1, wherein the reference sample signal comprises an elastic scattering spectrum resulting from illuminating a reference sample with the light source adjusted to the same setting used to generate the stored elastic scattering spectrum.

3. The method of claim 1, wherein the high output setting comprises a maximum intensity capable of being produced by the light source.

4. The method of claim 3, wherein the saturation threshold comprises a preset intensity level based on capabilities of the at least one optical detection sensor.

5. The method of claim 1, wherein the saturation threshold is 80% of the possible sensitivity of the at least one optical detection sensor.

6. The method of claim 1, wherein the low output setting comprises a level that is less than 25% of the maximum intensity capable of being produced by the light source.

7. The method of claim 2, wherein the reference sample comprises a material that exhibits diffuse reflectance.

8. The method of claim 1, wherein the light source comprises at least one discrete narrow-band light source.

9. The method of claim 1, wherein the light source comprises at least one broadband light source, and the at least one optical detection sensor comprises a charge coupled device (CCD).

10. The method of claim 1, wherein the light source comprises a fiber optic illumination source in contact with the skin lesion, wherein elastic scattering spectra are received from a fiber optic collector coupled to the at least one optical detection sensor.

11. The method of claim 1, further comprising performing image analysis on the skin lesion using at least one characteristic detection algorithm.

12. An elastic-Scattering Spectroscopy (ESS) system, comprising:
a light source;
an optical detection sensor;
a voltage divider circuit; and
a processor coupled to the at least one memory device, wherein the processor is configured with processor-executable instructions to:
illuminate a sample of the skin lesion with a first pulse from the light source adjusted to a high output setting;
receive a signal comprising an elastic scattering spectrum resulting from illuminating the sample of the skin lesion at the high output setting;
determine whether the received signal has an intensity that is greater than a saturation threshold associated with at least one optical detection sensor;
store the elastic scattering spectrum resulting from illuminating the sample of the skin lesion at the high output setting in response to determining that the received signal has an intensity greater than the saturation threshold; and
in response to determining that the received signal does not have an intensity greater than the saturation threshold:
illuminate the sample of the skin lesion with a second pulse from the light source adjusted to a low output setting;
receive a signal comprising an elastic scattering spectrum resulting from illuminating the sample of the skin lesion at the low output setting; and
store the elastic scattering spectrum resulting from illuminating the sample of the skin lesion at the low output setting.

13. The ESS system of claim 12, wherein the processor is further configured with processor-executable instructions to:
compute normalized spectral data for the sample of the skin lesion based on the stored elastic scattering spectrum and a reference sample signal,
wherein the reference sample signal comprises an elastic scattering spectrum resulting from illuminating a reference sample with the light source adjusted to the same setting used to generate the stored elastic scattering spectrum.

14. The ESS system of claim 12, wherein the saturation threshold comprises a preset intensity level based on capabilities of the at least one optical detection sensor.

15. The ESS system of claim 13, wherein the saturation threshold is 80% of the possible sensitivity of the at least one optical detection sensor.

16. The ESS system of claim 12, wherein the high output setting comprises a maximum intensity capable of being produced by the light source.

17. The ESS system of claim 12, wherein the low output setting comprises a level that is less than 25% of the maximum intensity capable of being produced by the light source.

18. The ESS system of claim 13, wherein the reference sample comprises a material that exhibits diffuse reflectance.

19. The ESS system of claim 12, wherein the light source comprises at least one broadband light source and the optical detection sensor comprises a charge coupled device (CCD).

* * * * *